United States Patent [19]

Nakata et al.

[11] Patent Number: 5,645,351
[45] Date of Patent: Jul. 8, 1997

[54] TEMPERATURE MEASURING METHOD USING THERMAL EXPANSION AND AN APPARATUS FOR CARRYING OUT THE SAME

[75] Inventors: Toshihiko Nakata, Hiratsuka; Shigeki Hirasawa, Ishioka; Yoko Saito, Tsukuba; Takanori Ninomiya, Hiratsuka; Mineo Nomoto, Yokohama, all of Japan

[73] Assignee: Hitachi, Ltd., Tokyo, Japan

[21] Appl. No.: 364,777

[22] Filed: Dec. 27, 1994

Related U.S. Application Data

[63] Continuation-in-part of Ser. No. 886,014, May 20, 1992, Pat. No. 5,377,006, and Ser. No. 994,150, Dec. 21, 1992, Pat. No. 5,479,259, which is a continuation-in-part of Ser. No. 886,014.

[30] Foreign Application Priority Data

Mar. 18, 1994 [JP] Japan ................................ 6-048314

[51] Int. Cl.⁶ .................................................. G01J 5/38
[52] U.S. Cl. .................................... 374/161; 374/120
[58] Field of Search ................................ 374/43, 45, 55, 374/120, 130, 137, 187, 161, 188; 356/349, 351, 355, 356, 357, 358

[56] References Cited

U.S. PATENT DOCUMENTS

| | | | |
|---|---|---|---|
| 4,381,152 | 4/1983 | Riech et al. | 374/55 |
| 4,521,118 | 6/1985 | Rosencwaig | 374/55 |
| 4,636,969 | 1/1987 | Kyoden et al. | 374/55 |
| 4,924,477 | 5/1990 | Gilmore et al. | 374/55 |
| 5,102,231 | 4/1992 | Loewenstein et al. | 374/120 |
| 5,221,142 | 6/1993 | Snow | 374/120 |
| 5,249,865 | 10/1993 | Paranjpe et al. | 374/120 |
| 5,350,899 | 9/1994 | Ishikawa et al. | 374/120 |
| 5,377,006 | 12/1994 | Nakata | 356/349 |
| 5,479,259 | 12/1995 | Nakata et al. | 356/357 |
| 5,539,520 | 7/1996 | Telle | 356/358 |

FOREIGN PATENT DOCUMENTS

| | | |
|---|---|---|
| 62-299037 | 12/1987 | Japan . |
| 1-129966 | 5/1989 | Japan . |

OTHER PUBLICATIONS

"Non-Invasive Process Temperature Monitoring Using Laser-Acoustic Techniques", Y. Lee et al, Center for Integrated Systems, Stanford, IEE 1990, pp. 105–106.

"Laser Generation of Convergent Acoustic Waves and Applications to Materials Evaluation", P. Cielo et al, Industrial Materials Research Institute, Canada, IEEE 1986, pp. 515–526.

*Primary Examiner*—G. Bradley Bennett
*Attorney, Agent, or Firm*—Antonelli, Terry, Stout & Kraus, LLP

[57] ABSTRACT

A temperature measuring method and apparatus for measuring temperature of at least one measuring point of a sample. At least one measuring point on a surface of a sample at least with a first light. A displacement of the at least one measuring point on the surface of the sample occurs from thermal expansion of the sample in response to the first light impinging thereon and a signal indicative of the displacement is produced. The temperature of the at least one measuring point of the sample is determined from the signal.

32 Claims, 10 Drawing Sheets

TEMPERATURE MEASURING METHOD USING THERMAL EXPANSION AND AN APPARATUS FOR CARRYING OUT THE SAME

CROSS-REFERENCE TO RELATED APPLICATIONS

This application is a continuation-in-part application of U.S. application Ser. No. 07/994,150, (now U.S. Pat. No. 5,479,259), filed Dec. 21, 1992, which is a continuation-in-part application of U.S. application Ser. No. 07/886,014, (now U.S. Pat. No. 5,377,006), filed May 20, 1992, and this application is a continuation-in-part application of copending U.S. application Ser. No. 07/886,014, the subject matter of the aforementioned parent applications being incorporated by reference herein.

BACKGROUND OF THE INVENTION

The present invention relates to a method of measuring the temperature of the surface of a solid, such as a silicon wafer for fabricating semiconductor devices, and a temperature measuring apparatus for carrying out the method. More particularly, the present invention relates to a method and apparatus of measuring the local temperature of a minute region on the order of square micrometers in a noncontact measuring mode.

A known noncontact temperature measuring apparatus for measuring the temperature of a silicon wafer, such as disclosed in Japanese Patent Laid-open (Kokai) No. 62-299037 or 1-129966, is a so-called radiation thermometer that uses a fact that the intensity of infrared rays emitted from the silicon wafer varies according to the temperature of the silicon wafer for measuring the temperature of the silicon wafer.

Another temperature measurement as described in "IEEE 1990 Symposium on VLSI Technology", pp. 105-106 (1990), discloses the temperature measurement of a silicon wafer by using a fact that the propagating velocity of a sound wave that propagates through or along the surface of a silicon wafer is dependent on the temperature of the silicon wafer.

When the radiation thermometer is used on a film forming apparatus, such as a semiconductor sputtering apparatus or a heat treatment apparatus, measured data includes errors because the emissivity of the silicon wafer is dependent on the process condition. Since the quantity of radiated infrared rays is proportional to the area of the point of measurement, the quantity of infrared rays radiated from a minute point of measurement having an area on the order of square micrometers is very small, which is difficult to measure.

The temperature measuring method using sound waves measures the average temperature of a portion of a length through which the sound wave propagates and is unable to measure the temperature of a minute are on the order of square micrometers.

SUMMARY OF THE INVENTION

It is an object of the present invention to provide a temperature measuring method and apparatus capable of accurately measuring the temperature of a minute point of measurement having an area on the order of square micrometers in the surface of a solid sample in a noncontact measuring mode.

In accordance with a feature of the present invention, a light beam emitted by a first light source is projected on a measuring point on the surface of a sample, a light beam emitted by a second light source is split into a probe light beam and a reference light beam, and the probe light beam is projected on the measuring point. The reflected probe light beam and the reference light beam are recombined to provide an interference light beam, and the interference light beam is detected by a detector. The intensity of the interference light beam is determined from the detection signal provided by the detector, a thermal expansion displacement of the sample is determined from the intensity of the interference light beam, and the temperature of the sample is determined from the thermal expansion displacement.

According to another feature of the present invention, a light beam emitted by a first light source is projected on a measuring point on the surface of a sample, a probe light beam emitted by a second light source is projected on a point slightly spaced from the measuring point, and the reflected probe light beam is detected by a position detector. The deflection of the reflected probe light beam is determined from the detection signal provided by the position detector, the thermal expansion displacement of the sample is determined from the deflection of the reflected probe light beam, and the temperature of the sample is determined from the thermal expansion displacement.

In accordance with a further feature of the present invention, a light beam having an intensity periodically varying at a desired frequency emitted by a first light source is projected on a measuring point on the surface of a sample, a light beam emitted by a second light source is split into a probe light beam and a reference light beam, and the probe light beam is projected on the measuring point. The reflected probe light beam and the reference light beam are recombined to provide an interference light beam, and the interference light beam is detected by a detector. The variation of the intensity of the interference light beam synchronous with the frequency is determined from the detection signal provided by the detector, a thermal expansion displacement of the sample is determined from the variation of intensity and the temperature of the sample is determined from the thermal expansion displacement.

According to another feature of the present invention, a light beam having an intensity periodically varying at a desired frequency emitted by a first light source is projected on a measuring point on the surface of a sample, a probe light beam emitted by a second light source is projected on a point slightly spaced from the measuring point, and the reflected probe light beam is detected by a position detector. The deflection of the reflected light synchronous with the frequency is determined from the detection signal provided by the position detector, the thermal expansion displacement of the sample is determined from the deflection and the temperature of the sample is determined from the thermal expansion displacement.

In accordance with the present invention, the light energy of the light beam projected on the measuring point on the surface of the sample is converted into thermal energy, which causes a thermal expansion displacement along the optical axis of the light beam (photothermal displacement effect). When a light beam emitted by a light source is split into a probe light beam and a reference light beam, and the probe light beam is projected on the measuring point, the phase of the reflected probe light is dependent on the thermal expansion displacement along the optical axis. Therefore, when the reflected probe light beam and the reference light beam are recombined to provide an interference light beam, the intensity of the interference light beam varies according to the thermal expansion displacement. That is, the thermal expansion displacement can be determined from the intensity of the interference light beam. The thermal expansion displacement is dependent on the thermal conductivity and the linear expansion coefficient of the sample, and the thermal conductivity and the linear expansion coefficient are dependent on the local temperature so that the local temperature of the measuring point can be calculated on the basis of the thermal expansion displacement.

When the probe light beam is projected on a point slightly spaced from the measuring point, namely, on a minute slope formed in the surface of the sample by the thermal expansion along the optical axis, the probe light beam is reflected in a direction different from the direction of incidence, and the deflection of the reflected probe light beam changes according to the magnitude of the thermal expansion displacement. Accordingly, the thermal expansion displacement can be determined from the deflection. Since the thermal expansion displacement is dependent on the thermal conductivity and the linear expansion coefficient of the sample and both the thermal conductivity and the linear expansion coefficient are dependent on the local temperature of the sample, the local temperature of the measuring point can be calculated on the basis of the thermal expansion displacement.

When the light beam having an intensity periodically varying at a desired frequency is projected on the measuring point on the surface of the sample, the light energy is converted into thermal energy and periodical thermal expansion displacement synchronous with the desired frequency occurs along the optical axis of the light beam (photothermal displacement effect). When a light beam emitted by a light source is split into a probe light beam and a reference light beam, and the probe light beam is projected on the measuring point, the phase of the reflected probe light beam varies periodically according to the variation of the thermal expansion displacement along the optical axis. When the reflected probe light beam and the reference light beam are recombined to provide an interference light beam, the intensity of the interference light beam varies periodically in synchronism with the thermal expansion displacement. That is, the thermal expansion displacement can be determined from the variation of the intensity of the interference light beam. Since the variation of the thermal expansion displacement is dependent on the thermal conductivity and the linear expansion coefficient of the sample and the thermal conductivity and the linear expansion coefficient are dependent on the local temperature of the sample, the local temperature of the measuring point can be calculated on the basis of the thermal expansion displacement.

When the probe light beam is projected on a point slightly spaced from the measuring point, i.e., a minute slope on the surface of the sample formed by the thermal expansion displacement along the optical axis, the reflected probe light beam travels along a direction different from the direction of incidence and the deflection varies periodically in synchronism with the variation of the thermal expansion displacement. Accordingly, the thermal expansion displacement can be determined from the deflection. Since the thermal expansion displacement is dependent on the thermal conductivity and the linear expansion coefficient of the sample, and the thermal conductivity and the linear expansion coefficient are dependent on the local temperature of the sample, the local temperature of the measuring point can be calculated on the basis of the thermal expansion displacement.

Other objects and features of the present invention will become apparent by reference to the following description and drawings.

DESCRIPTION OF THE PREFERRED EMBODIMENTS

Figure 1:
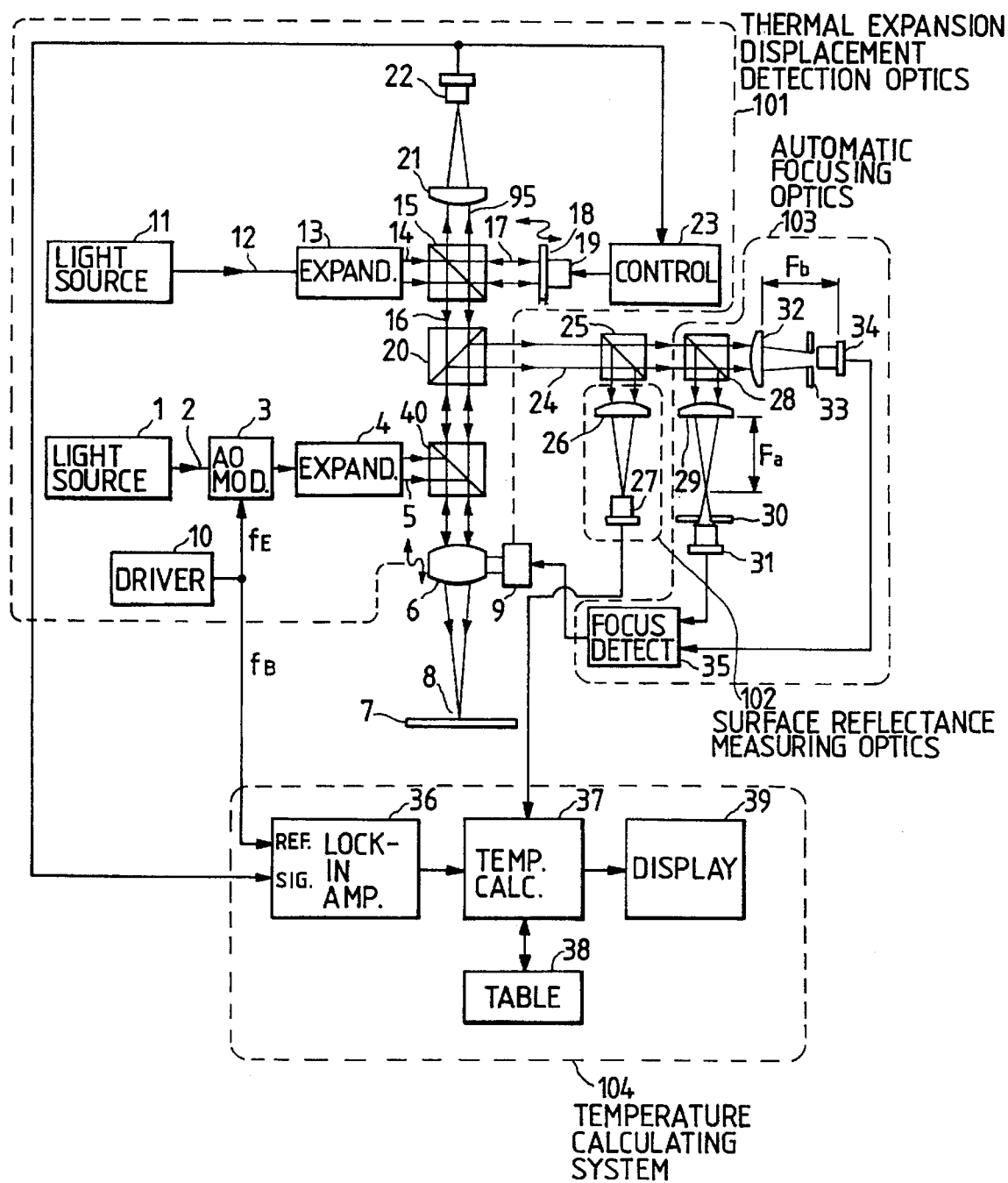
FIG. 1 is a block diagram of a temperature measuring apparatus according to a first embodiment of the present invention.

Referring now to the drawings wherein like reference numerals are utilized to designate like parts throughout the various figures, a first embodiment will be described with reference to FIGS. 1–6, wherein FIG. 1 is a block diagram of a temperature measuring apparatus according to the present invention.

The temperature measuring apparatus comprises a thermal expansion displacement detecting optical system 101, a surface reflectance measuring optical system 102, an automatic focusing optical system 103 and a temperature data processing system 104.

Figure 2:
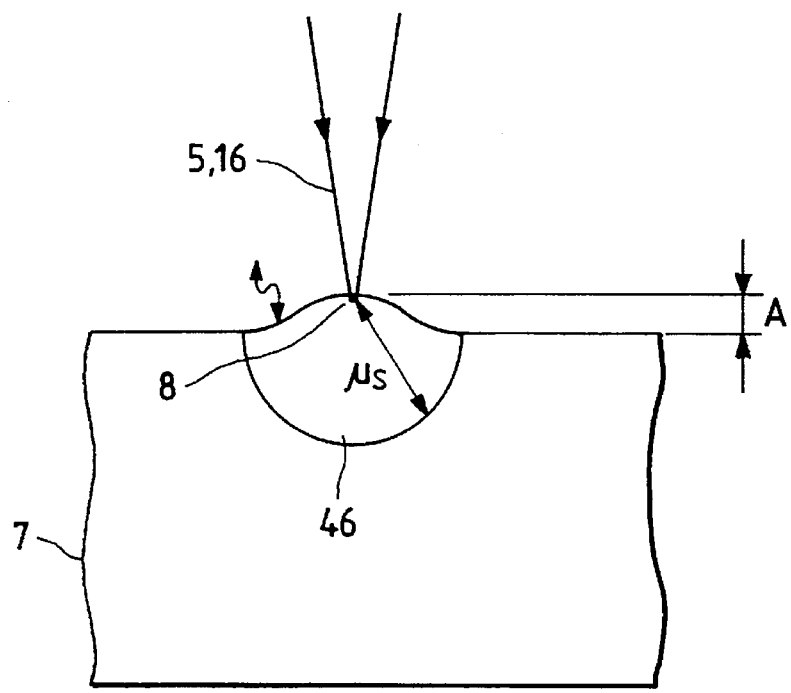
FIG. 2 is a sectional view of a sample, showing a periodically varying thermal expansion displacement caused by an intensity-modulated exciting light beam of FIG. 1.

In the thermal expansion displacement detecting optical system 101, the intensity of a light beam 2 of 514.5 nm in wavelength emitted by a light source 1, such as an Ar laser, is modulated by a modulating frequency $f_E$ by an acoustooptic modulating device 3 driven by a driving signal having a frequency $f_E$ provided by a driver 10, the intensity-modulated light beam is expanded by a beam expander 4 to provide an expanded light beam 5, the expanded light beam 5 is reflected as an excitation light beam by a dichroic prism 40 that reflects light of 600 nm or below in wavelength and transmits light of 600 nm or above in wavelength, and the reflected light beam is focused on a measuring point 8 on a sample 7 with an objective lens system 6. When the N.A. of the objective lens 6 is 0.42, the diameter of the spot of the excitation light beam 5 is about 1.5 μm, which enables the measurement of the temperature of a minute point of measurement having an area on the order of square micrometers. As shown in FIG. 2, a periodic thermal expansion displacement of an amplitude A occurs in the surface of the sample at the measuring point 8 in synchronism with the modulating frequency $f_E$. The light energy of the excitation light beam 5 absorbed by the sample is converted into thermal energy and the thermal energy is diffused in a thermal diffusion region 46. The thermal diffusion length μs is expressed by:

$$\mu s = \sqrt{\kappa / \pi f_E \rho c} \qquad (1)$$

where $f_E$ is modulating frequency, κ is the thermal conductivity of the sample 7, ρ is the density of the sample 7, and c is the specific heat of the sample 7.

For example, when the sample 7 is formed of silicon and the modulating frequency $f_E$ is 88 kHz, the thermal diffusion length μs is 18 μm. The modulating frequency is selected based upon the properties or type of the sample and the desired spatial resolution.

On the other hand, a beam 12 emitted by a coherent light source 11 (wavelength=633 nm), such as a He-Ne laser, is expanded by a beam expander 13 to provide an expanded beam 14, and the expanded beam 14 is split into beams 16 and 17 by a beam splitter 15. The beam 16 is used as a probe light beam, and the beam 17 is used as a reference light beam. The beam 16 is passed through a beam splitter 20 and the dichroic prism 40 and is focused by the objective 6 on the measuring point 8 on the sample 7 on which the excitation light beam 5 is focused. When the N.A. of the objective 6 is 0.42, the diameter of the spot of the probe light 16 is about 1.8 μm, which enables the measurement of the temperature of a minute point of measurement having an area on the order of square micrometers. The phase of the reflected probe light 16 reflected by the measuring point 8 is caused to vary periodically at the frequency $f_E$ by the periodic thermal expansion displacement. The reflected probe beam 16 travels in the reverse direction along the same optical path and is recombined with the reference beam 17 reflected by a reference mirror 18 by the beam splitter 15, so that the reflected probe beam 16 and the reflected reference beam 17 interfere with each other. The intensity of the interference light varies periodically in synchronism with the periodically varying thermal expansion displacement. The interference light 95 is concentrated by a condenser lens 21 on a photoelectric conversion device 22, such as a photodiode. The intensity I of the interference light beam is expressed by:

$$I = I_s + I_R + 2\sqrt{I_s I_R} \cos\{(4\pi A/\lambda) \cos(2\pi f_E t + \theta) + \phi\} \qquad (2)$$

where λ is the wavelength of the probe light beam, $I_s$ is the intensity of the reflected probe light beam, $I_R$ is the intensity of the reflected reference light beam, A is the amplitude of thermal expansion displacement, θ is the phase lag of the thermal expansion displacement, and φ is the phase difference based on the difference between the optical path of the probe light beam and that of the reference light beam.

An interference signal provided by the photoelectric conversion device 22 is given to a lock-in amplifier 36 included in the temperature data processing system 104. The modulating signal having the frequency $f_E$ provided by the driver 10 for the intensity modulation of the exciting light beam is applied to the lock-in amplifier 36. The amplitude A of the frequency $f_E$ of the interference signal and the phase lag θ are determined by synchronous detection using the modulating signal having the frequency $f_E$ as a reference signal. Since the amplitude A and the phase lag θ are in one-to-one correspondence with the amplitude and the phase lag of the thermal expansion component, at least the amplitude A is used as the amplitude of the thermal expansion component in the following signal processing.

Figure 3:
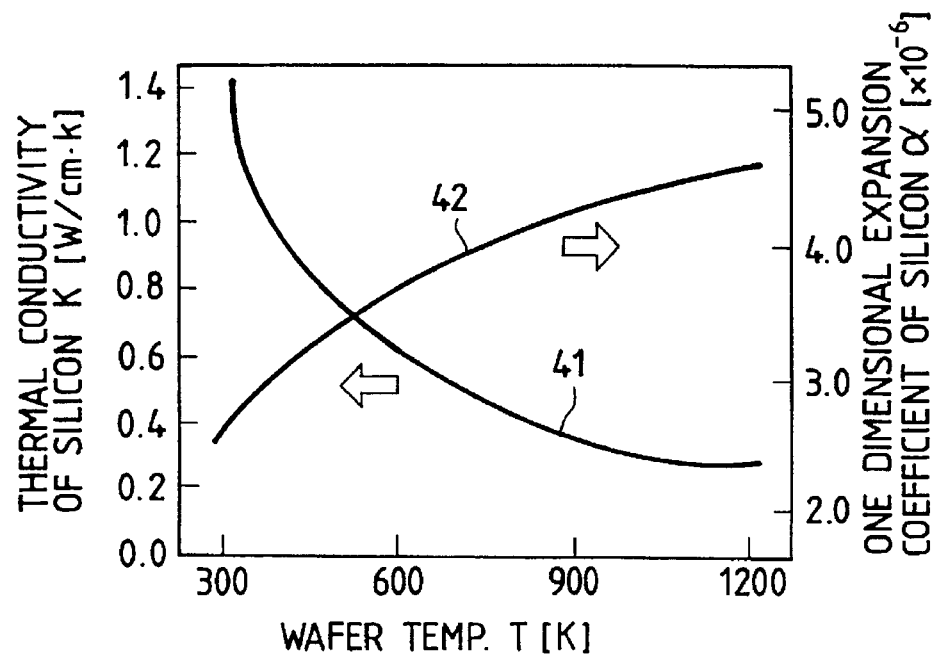
FIG. 3 is a graph showing the variation of the thermal conductivity κ and the variation of the one dimensional or linear expansion coefficient α of silicon with temperature T of a silicon wafer.
Figure 4:
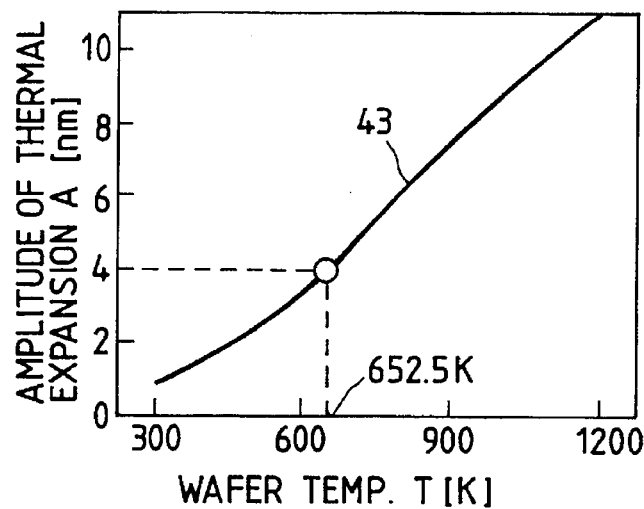
FIG. 4 is a graph showing the variation of thermal expansion amplitude A with the temperature T of a silicon wafer.

FIG. 3 shows the relation between the temperature T of a silicon wafer for fabricating a semiconductor device, the thermal conductivity κ coefficient of silicon and the linear expansion coefficient α of silicon. The thermal conductivity κ is inversely proportional to the temperature T of the wafer, and the linear expansion coefficient α increases gradually with the increase of the temperature T. Generally, the amplitude A of thermal expansion is inversely proportional to thermal conductivity K and directly proportional to a one-dimensional or linear expansion coefficient α as expressed by expression (3).

$$A \propto P \cdot (\alpha/\kappa) \qquad (3)$$

where P is the energy of exciting light beam 5 absorbed by the sample. From FIG. 3 and expression (3), the relation between the temperature T of the wafer and the amplitude A of thermal expansion can be represented by a graph as shown in FIG. 4. Therefore, a reference table representing the theoretically or empirically determined relation between the temperature T of the wafer and the amplitude A of thermal expansion is stored beforehand in a memory or the like, and the temperature T of the wafer corresponding to a measured amplitude A can be found on the reference table. For example, when the amplitude A of thermal expansion is 4 nm, a corresponding temperature T of the wafer is 652.5K (Kelvin). In FIG. 1, a reference table 38 is included in the temperature data processing system 104. The amplitude A of thermal expansion determined by the lock-in amplifier 36 is supplied to a temperature calculating circuit 37, and then the temperature calculating circuit 37 searches the reference table 38 for a temperature T corresponding to the amplitude A of thermal expansion, and then the temperature T is displayed on a display 39.

On the other hand, the interference signal provided by the photoelectric conversion device 22 is supplied also to a reference mirror control circuit 23. Then, the reference mirror control circuit 23 drives a PZT device 19 to adjust the position of a reference mirror 18 minutely with respect to the direction of the optical axis so that the contrast of the periodic variation of the interference signal synchronous with the thermal expansion displacement is always a maximum. More concretely, the reference mirror 18 is adjusted so that φ of expression (2) is always π/2.

Part of the reflected probe light beam 16 is reflected by the beam splitter 20 and split into a first reflected probe beam and a second reflected probe beam by a beam splitter 25. The first reflected probe beam is guided to the surface reflectance measuring optical system 102 and is concentrated by a condenser lens 26 on a photoelectric conversion device 27, such as a photodiode. As is apparent from expression (2), the intensity of the interference signal varies according to the intensity of the reflected probe light beam, i.e., the reflectance of the surface of the sample. Therefore, the output signal of the photoelectric conversion device 27 is supplied as a reflectance correction signal to the temperature calculating circuit 37 included in the temperature data processing system 104 to correct the surface reflectance in calculating the temperature on the basis of the thermal expansion displacement.

The second reflected probe beam provided by splitting the reflected probe beam is guided to the automatic focus detecting optical system 103, in which the second reflected probe beam is split into two split beams by a beam splitter 28. The split beams are concentrated by condenser lenses 29 and 32 on photoelectric conversion devices 31 and 34, such as photodiodes, disposed behind pinholes 30 and 33, respectively. The distances between the condenser lens 29 and the pin hole 30 and the photoelectric conversion device 31 are longer than the focal distance Fa of the condenser lens 29, and the distances between the condenser lens 32 and the pin hole 33 and the photoelectric conversion device 34 are shorter than the focal distance Fb of the condenser lens 32. The respective positions of the photoelectric conversion devices 31 and 34 are adjusted so that the respective intensities of the output signals of the photoelectric conversion devices 31 and 34 are equal to each other when the intensity-exciting light beam 5 and the probe light beam 16 are concentrated in minimum spots on the measuring point 8 on the sample 7, i.e., when the exciting light beam 5 and the probe light beam 16 are focused on the measuring point 8 on the sample 7 by the objective 6.

The output signals of the photoelectric conversion devices 31 and 34 are supplied to an automatic focus detecting circuit 35. If the objective 6 deviates from a focusing position for focusing the probe light beam on the surface of the sample 7, the respective intensities of the output signals of the photoelectric conversion devices 31 and 34 are different from each other, and the direction of deviation of the objective 6 relative to the sample 7 can be determined from the comparison of the different intensities of the output signals of the photoelectric conversion devices 31 and 34. The automatic focus detecting circuit 35 compares the intensities of the two output signals of the photoelectric conversion devices 31 and 34 continuously, and supplies a driving signal to the objective actuator 9 comprising a PZT element to adjust the position of the objective 6 so that the respective intensities of the output signals of the photoelectric conversion devices 31 and 34 coincide with each other and, consequently, the exciting light beam 5 is always concentrated in a spot of a minimum diameter so that the sample absorbs energy at a constant rate. Consequently, stable thermal expansion displacement occurs to improve the accuracy of temperature measurement. Since the probe light beam 16 is concentrated always in a spot of a minimum diameter, the temperature of a minute point of measurement having an area on the order of square micrometers can be measured with high measuring accuracy.

Figure 5:
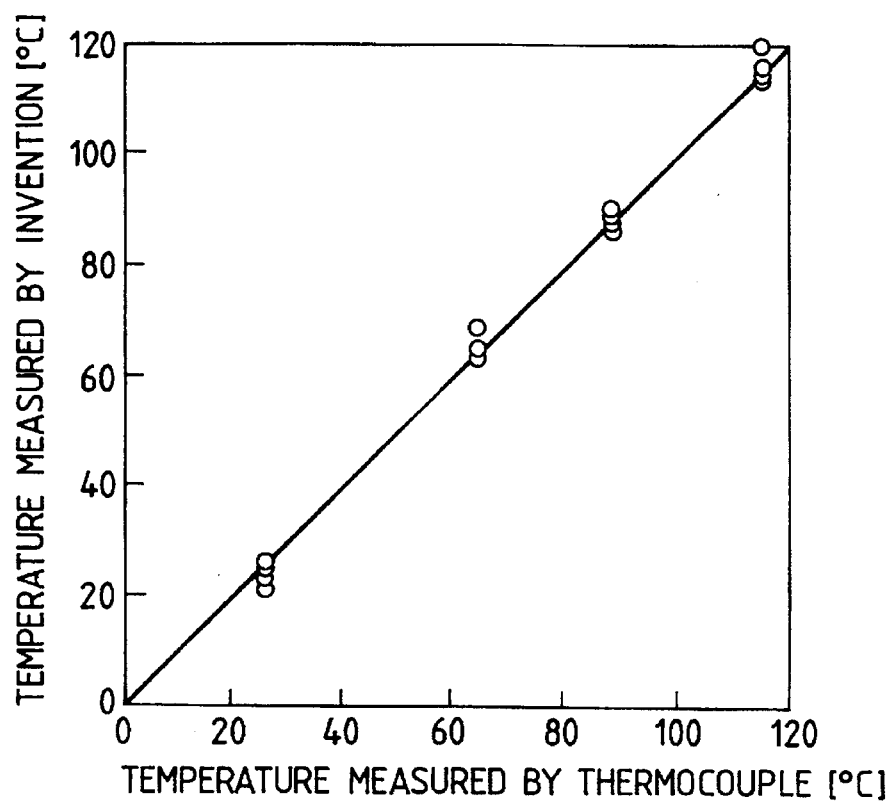
FIG. 5 is a graph showing the relation between measured temperature measured by a thermocouple and measured temperature measured by the temperature measuring apparatus in accordance with the first embodiment.

FIG. 5 is a graph showing the relation between the temperature of a silicon wafer measured with a thermocouple in a contact measuring mode and that of the same silicon wafer measured with the temperature measuring apparatus of the present invention, shown in FIG. 1, in a noncontact measuring mode. The measurements obtained by the thermocouple can be regarded as the true temperature of the silicon wafer. As is apparent from FIG. 5, the measuring accuracy of the temperature measuring apparatus of the present invention is ±10° C. with regard to the temperature measured by the thermocouple.

The temperature measuring accuracy is dependent mainly on the accuracy of measurement of thermal expansion displacement. For example, the temperature measuring accuracy of the temperature measuring apparatus of the present invention shown in FIG. 1 is ±10° C. when the accuracy of measurement of thermal expansion displacement is on the order of 0.1 nm. If the effect of noise, such as vibration and fluctuation of air, is reduced, the accuracy of measurement of thermal expansion displacement is improved to 0.01 nm, and the accuracy of temperature measurement will be enhanced to ±1° C., which is far higher than the accuracy of the conventional noncontact temperature measuring method.

Furthermore, as mentioned above, the exciting light beam and the probe light beam can be concentrated in a small spot having a diameter on the order of micrometers to enable the measurement of the temperature of a minute point of measurement having an area on the order of square micrometers.

In the embodiment of FIG. 1, for example, the thermal expansion displacement detecting optical system 101 modulates the intensity of the light beam 2 emitted by the light source 1 (wavelength=514.5 nm), such as an Ar laser, by the acoustooptic modulating device 3 by the modulating frequency $f_E$ to provide the intensity-modulated beam 5 as an exciting light beam, and concentrates the intensity-modulated beam 5 on the measuring point 8 on the sample 7. However, the acoustooptic modulating device 3 may be omitted and a light beam having a fixed intensity may be used as an exciting light beam. In such a case, the driver 10 and the lock-in amplifier 36 are unnecessary and the interference signal provided by the photoelectric conversion device 22 is directly supplied to the temperature calculating circuit 37. With such arrangement, first, the initial thermal expansion displacement of the measuring point 8 is measured by light interference before irradiating the measuring point 8 with an exciting light beam in a manner similar to that of the first embodiment. Then, an exciting light beam is projected on the measuring point 8. The thermal expansion displacement starts increasing as soon as the measuring point 8 is irradiated with the exciting light beam and reaches a fixed thermal expansion displacement in a certain time. Then, the steady-state thermal expansion displacement is measured again by light interference. The initial thermal expansion displacement is subtracted from the steady-state thermal expansion displacement to obtain the differential thermal expansion displacement. Then, reference is made to the relation between the temperature T of the sample 7 and the differential thermal expansion displacement, as shown in FIG. 4, stored in the table 38 beforehand to find a wafer temperature T corresponding to the differential thermal expansion displacement. The temperature T thus determined is displayed on the display 39. If the thermal expansion displacement is measured always a fixed time after the start of irradiation with the exciting light beam, the transient thermal expansion displacement is measured and the transient thermal expansion displacement may be used for determining the temperature.

Figure 6:
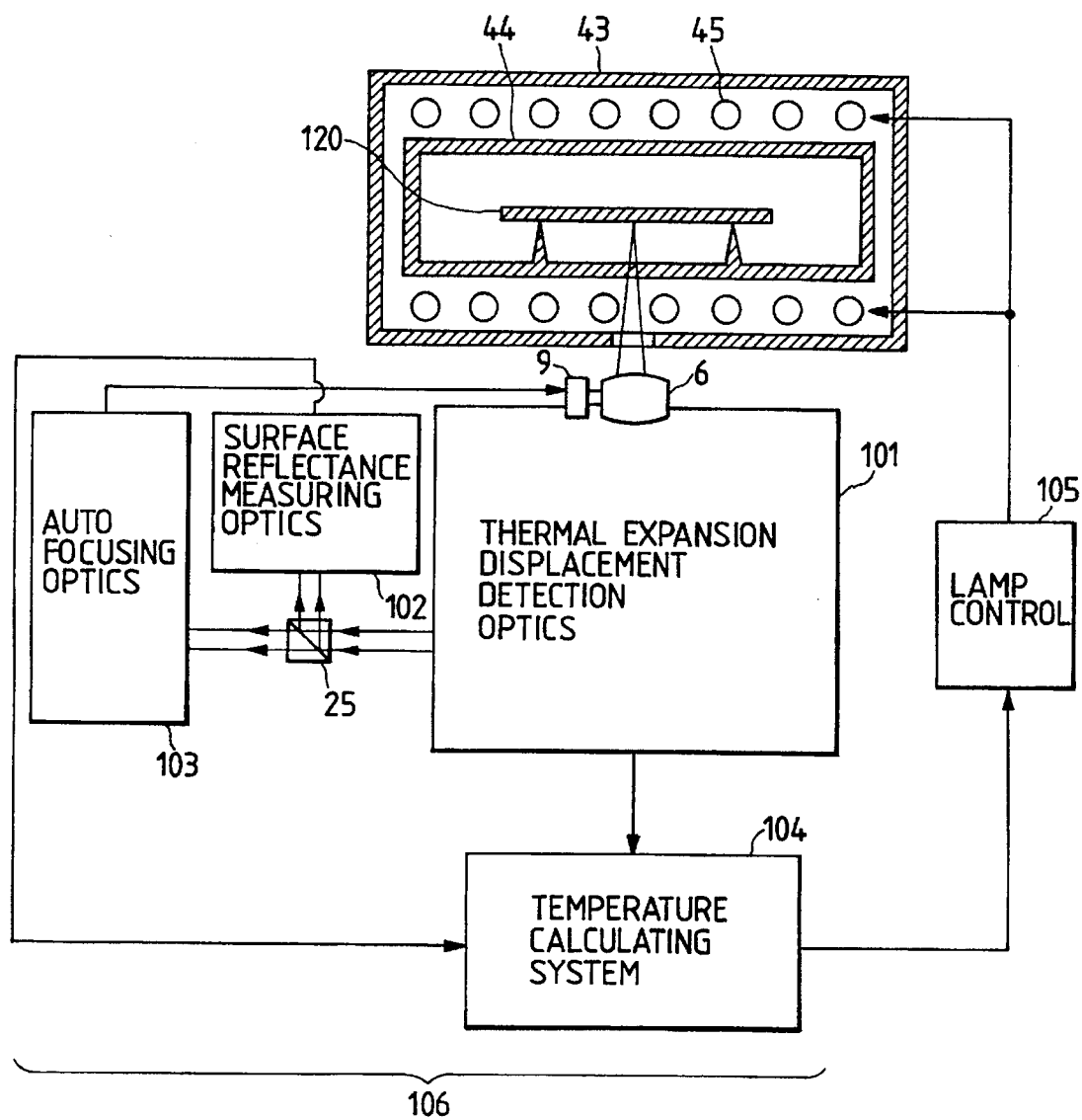
FIG. 6 is a block diagram of a combination of the temperature measuring apparatus in the first embodiment and a semiconductor heat-treating apparatus of a lamp-heating system according to the present invention.

FIG. 6 is a block diagram of a semiconductor heat treatment apparatus of a lamp-heating system incorporating a temperature measuring apparatus 106 of the present invention. The temperature measuring apparatus 106, similarly to that shown in FIG. 1, comprises a thermal expansion displacement detecting optical system 101, a surface reflectance measuring optical system 102, an automatic focus detecting optical system 103, a temperature data processing system 104 and a lamp control system 105. In the semiconductor heat treatment apparatus, a silicon wafer 120 is contained in a reaction tube 44 of quartz glass, a plurality of heating halogen lamps 45 are arranged around the reaction tube 44, and the reaction tube 44 and the heating halogen lamps 45 are surrounded by reflecting walls 43. A process gas, such as oxygen gas, is supplied into the reaction tube 44 and the wafer 120 is heated with the heating light emitted by the halogen lamps 45 at about 900° C. for about one minute to form a thin film, such as a thin $SiO_2$ film, over the surface of the wafer 120.

The temperature of the wafer 120 is measured accurately by the temperature measuring apparatus 106 of the present invention. The temperature data processing system 104 provides a measured temperature signal to the lamp control system 105 to control the heating value of the halogen lamps 45 with high accuracy, so that the wafer 120 is maintained at a predetermined temperature with high accuracy. Consequently, a thin film having a satisfactory film quality can be formed over the surface of the wafer 120 with an accurate thickness. Since the thin film is formed also over the measuring point on the wafer 120 during the thin film forming process, the surface reflectance changes due to multiple interference within the thin film. The surface reflectance measuring optical system 102 corrects the change in the surface reflectance to enable accurate temperature measurement.

Although the described embodiments measure the temperature of the sample at a single measuring point, a plurality of exciting light beams and a plurality of probe light beams may be used or the temperature distribution on the surface of the sample may be measured by two-dimensionally scanning the surface of the sample, and by using a plurality of photoelectric conversion devices or an array of a plurality of photoelectric conversion elements, such as a CCD and a temperature distribution is obtainable. When the temperature measuring apparatus is applied to the semiconductor heat treatment apparatus of a lamp-heating system, it is possible to heat the silicon wafer in a uniform temperature distribution by controlling the heating value of each halogen lamp individually according to the temperature distribution on the surface of the silicon wafer, so that a thin film with high film quality can be formed with an accurate thickness over the entire surface of the wafer, which is very effective in forming a thin film over the surface of a silicon wafer having a large area.

The temperature measuring apparatus in the embodiment of FIG. 6 is not limited to application to a semiconductor heat treatment apparatus of a lamp-heating system, and may be applied to a film forming apparatus for forming a thin film in fabricating semiconductor devices, such as a sputtering apparatus. It is also possible to apply the temperature measuring apparatus to a dry etching apparatus to etch the surface of a wafer uniformly by heating the wafer with a uniform temperature distribution.

Figure 7:
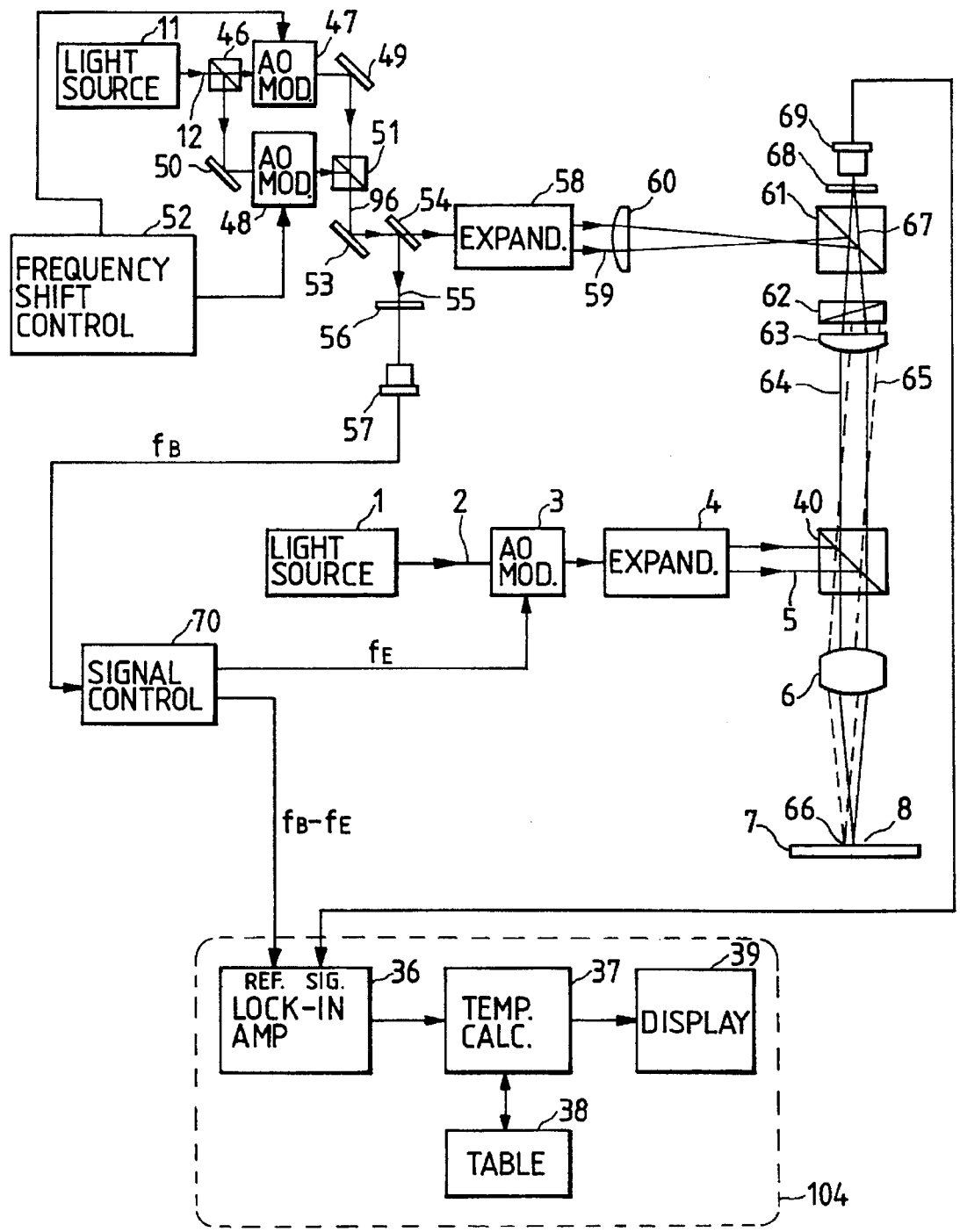
FIG. 7 is a block diagram of a temperature measuring apparatus according to another embodiment of the present invention.
Figure 8:
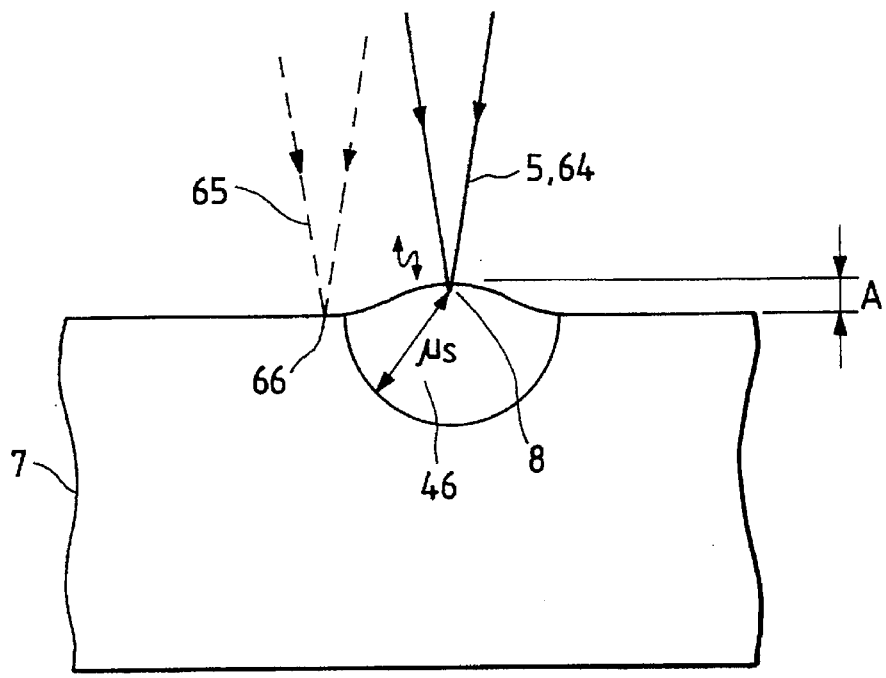
FIG. 8 is a sectional view of a sample, showing a mode of causing periodic thermal expansion displacement by an exciting light beam, and positions at which a probe light beam and a reference light beam fall on the sample in accordance with FIG. 7.

A temperature measuring apparatus in another embodiment according to the present invention will be described with reference to FIGS. 7 and 8, wherein FIG. 7 is a block diagram of the temperature measuring apparatus. The temperature measuring apparatus comprises a thermal expansion displacement detecting optical system 107 and a temperature data processing system 104. While the temperature measuring apparatus in the first embodiment employs a Michelson interferometer including a reference mirror, the temperature measuring apparatus in this embodiment is featured by a common path interferometer not provided with any reference mirror.

The thermal expansion displacement detecting optical system of this embodiment, similarly to that of the first embodiment, modulates the intensity of a light beam 2 emitted by a light source 1 (wavelength=514.5 nm), such as an Ar laser, by a modulating frequency $f_E$ by an acoustooptic modulating device 3, expands the intensity-modulated light beam by a beam expander 4 to provide an expanded light beam 5, reflects the expanded light beam 5 as an exciting light beam which is reflected by a dichroic prism 40, which reflects light of wavelengths of 600 nm or below and transmits light of wavelengths of 600 nm or above, and concentrates the reflected, expanded light beam 5 on a measuring point 8 on a sample 7 with an objective 6. When the N.A. of the objective 6 is 0.42, the diameter of the spot of the exciting light beam on the sample is about 1.5 μm, which is small enough for the measurement of the temperature of a minute point of measurement having an area on the order of square micrometers. As shown in FIG. 8, the photothermal displacement effect causes an expansion displacement that varies periodically at a frequency $f_E$ in an amplitude A at the measuring point 8.

A linearly polarized light beam 12 emitted by a coherent light source 11 (wavelength=633 nm), such as a He-Ne laser, falls on a polarization beam splitter 46 at a polarizing angle of 45°. The polarization beam splitter 46 splits the incident light beam into a p-polarized light beam and an s-polarized light beam. A light frequency shift control circuit 52 drives acoustooptic modulating devices 47 and 48 to subject the p-polarized light beam transmitted through the polarized light beam splitter 46 to a light frequency shift of $f_1$ by an acoustooptic modulating device 47 and to subject the s-polarized light beam reflected by the polarized light beam splitter 46 to light frequency shift of $f_2$ ($f_1 \neq f_2$) by an acoustooptic modulating device 48. The polarized beams are recombined by a polarized light beam splitter 51 to obtain a two-frequency orthogonal beam 96 having polarizing directions perpendicular to each other and frequencies differing from each other by $f_1-f_2$.

Part of the two-frequency orthogonal beam 96 is reflected by the beam splitter 54, the reflected two-frequency orthogonal beam is subjected to polarization interference by a polarizing plate 56 disposed at 45°, and a heterodyne interference light beam having a beat frequency $f_B=f_1-f_2$ falls on a photoelectric conversion device 57. The beat signal having the frequency $f_B$ is sent to a signal control circuit 70 and is used as a reference signal for generating an intensity modulating signal of a frequency $f_E$ for the exciting light beam by using a frequency dividing circuit and a PLL (phase locked loop) and for generating a reference signal of a frequency $f_B-f_E$ to be used in extracting the thermal expansion component from an interference signal.

The two-frequency orthogonal beam 96 is expanded by a beam expander 58 to provide an expanded beam 59 which is concentrated by a lens 60. The concentrated expanded beam 59 is reflected by a beam splitter 61, and the reflected expanded beam 59 is converted into a parallel beam by a lens 63. A birefringence prism 62 of calcite or the like, such as a Savart plate, is disposed immediately before the lens 63 to split the two-frequency orthogonal beam 59 into a p-polarized light beam 64 and an s-polarized light beam 65. The p-polarized beam 64 (shown in solid lines) is transmitted through a dichroic prism 40 and is concentrated by an objective 6 on the measuring point 8 on which the exciting light beam 5 is concentrated. When the N.A. of the objective 6 is 0.42, the diameter of the spot of the probe light beam 16 is about 1.8 μm, which enables the measurement of the temperature of a minute point of measurement having an area on the order of square micrometers. On the other hand, the s-polarized light beam 65 (shown in broken lines) is transmitted through the dichroic prism 40 and is concentrated by the objective 6 as a reference light beam on a point 66 slightly spaced from the measuring point 8, as shown in FIG. 8. The point 66 on which the s-polarized light beam falls is outside an area in which thermal expansion displacement occurs, namely, at a distance equal to or greater than a thermal diffusion length, for example about 1.8 µm or above when the modulating frequency $f_E$=88 kHz, from the measuring point 8, i.e., the point on which the probe light beam (p-polarized light beam 64) falls.

The phase of the reflected probe light beam 64 reflected by the measuring point 8 varies periodically at the frequency $f_E$ due to periodic thermal expansion displacement. The reflected probe light beam 64 and the reflected reference light beam 65 travel along the same optical path and are recombined by the birefringence prism 62 (such as a Savart plate). The recombined reflected light beam 67 is transmitted through the beam splitter 61 and is subjected to heterodyne polarization interference by a polarizing plate 68 disposed at 45° to the directions of polarization of the reflected light beams. The intensity of the interference light beam varies periodically in synchronism with the periodic variation of the thermal expansion displacement. The interference light is concentrated by the lens 63 on a photoelectric conversion device 69, such as a photodiode. The intensity I of the interference light beam is expressed by:

$$I=(I_s+I_R)+2\sqrt{I_s I_R}[\cos(2\pi((f_B t+\phi)+(2\pi/\lambda)A \sin\{2\pi(f_B+f_E)t+\phi+\theta\}+ (2\pi/\lambda)A \sin\{2\pi(f_B-f_E)t+\phi-\theta\}] \quad (4)$$

where $\lambda$ is the wavelength of the probe light beam, $I_s$ is the intensity of the reflected probe light beam, $I_R$ is the intensity of the reflected reference light beam, $f_B=f_1-f_2$ is the difference between the respective frequencies of the reflected probe light beam and the reflected reference light beam, A is the amplitude of thermal expansion displacement, $\theta$ is the phase lag of the thermal expansion displacement, and $\phi$ is the phase difference due to the difference between the optical path of the probe light beam and that of the reference light beam.

The first term is a dc component, the second term is a component of the frequency $f_B$, the third term is a thermal expansion component of the frequency $f_B+f_E$, and the fourth term is a thermal expansion component of the frequency $f_B-f_E$. A component to be determined is the third or the fourth term.

This embodiment extracts the fourth term, i.e., the thermal expansion component of the frequency $f_B-f_E$. The interference signal provided by the photoelectric conversion device 69 is supplied to a lock-in amplifier 36 included in the temperature data processing system 104. The lock-in amplifier 36 determines the amplitude A and the phase lag $\theta$ of the thermal expansion component of the frequency $f_B-f_E$ included in the interference signal by synchronous detection using the signal of the frequency $f_B-f_E$ generated by the signal control circuit 70 as a reference signal.

Similarly to the operation of the first embodiment, the amplitude A of thermal expansion determined by the lock-in amplifier 36 is supplied to the temperature calculating circuit 37, the temperature calculating circuit 37 searches a table 38 showing the relation between the temperature T of the wafer and the amplitude A of thermal expansion, as shown in FIG. 4, to find a temperature T of the wafer corresponding to the amplitude A of thermal expansion, and then the display 39 displays the temperature T.

The temperature measuring apparatus in the aforementioned embodiment, similarly to the temperature measuring apparatus in the first embodiment, is capable of noncontact measurement of the temperature of a minute point of measurement having an area on the order of square micrometers with high accuracy. Additionally, a plurality of light beams or scanning light beams may be utilized to obtain a temperature distribution.

The temperature measuring apparatus in the aforementioned embodiment employs a common path interferometer using the surface of the sample as a reference surface and hence the respective optical paths of the reference light beam and the probe light beam are substantially the same. Therefore, the temperature measuring performance of the temperature measuring apparatus is hardly affected by disturbances, such as vibration of the optical systems and the samples, and the change and the fluctuation of the refractive index of the gas surrounding the sample.

The measuring accuracy of the temperature measuring apparatus in the aforementioned embodiment, similarly to that of the temperature measuring apparatus in the first embodiment, can be improved by additionally including a surface reflectance measuring optical system 102 and an automatic focus detecting optical system 103.

The temperature measuring apparatus in the aforementioned embodiment, similarly to the temperature measuring apparatus in the first embodiment, is applicable to a semiconductor heat-treating apparatus of a lamp-heating system, a sputtering apparatus and an etching apparatus for the same effect. When the temperature measuring apparatus is applied to a semiconductor heat-treating apparatus of a lamp-heating system, it is expected that the optical path length changes due to the change of the refractive index of the gas filling up the reaction tube when the gas is heated and the measured interference intensity includes an error. However, since respective optical paths of the reference light beam and the probe light beam in this temperature measuring apparatus are substantially the same, the measured interference intensity is hardly affected by the change of optical path length, so that the thermal expansion displacement can be detected with high accuracy.

In the thermal expansion displacement detecting optical system 107 in this embodiment, the intensity of the light beam 2 emitted by the light source (wavelength=514.5 nm), such as an Ar laser, is modulated by the modulating frequency $f_E$ by the acoustooptic modulating device 3, and the intensity-modulated light beam 5 as an exciting light beam is concentrated on the measuring point 8 on the sample 7. As explained in connection with the first embodiment, the acoustooptic modulating device 3 may be omitted and the a light beam having a fixed intensity may be used as an exciting light beam. In such a case, the beat signal of a frequency $f_B$ detected by the photoelectric conversion device 57 is sent through the signal control circuit 70 to the lock-in amplifier 36 to use the same as a reference signal.

Since this embodiment employs the common path interferometer that uses a portion of the surface of the sample spaced from the measuring point as a reference surface, the detected thermal expansion displacement is caused only by the exciting light beam. Accordingly, as mentioned above, the thermal expansion displacement need not be measured twice before and after irradiation with the exciting light beam. When the measuring point 8 is irradiated with the exciting light beam, the measuring point 8 starts expanding immediately, the thermal expansion displacement increases with time, the thermal expansion reaches a steady state in a certain time and, thereafter, the thermal expansion displacement remains constant. After the thermal expansion has reached a steady state, the thermal expansion displacement is measured by light interference. Since the interference signal detected by the photoelectric conversion device 69 includes only the frequency component of the frequency $f_B$, the thermal expansion displacement can be detected by applying the interference signal to the lock-in amplifier 36 and using the beat signal of the frequency $f_B$ provided by the signal control circuit 70 as a reference signal. The reference table 38 storing the relation between the temperature T of the sample 7 and the thermal expansion displacement, as shown in FIG. 4, is searched for a temperature T corresponding to the measured thermal expansion displacement to determine the temperature T of the wafer. The temperature T thus determined is displayed on the display 39. The transient thermal expansion displacement may be measured a fixed time after starting the irradiation of the sample with the exciting light beam, and the temperature of the sample may be estimated on the basis of the transient thermal expansion displacement.

Figure 9:
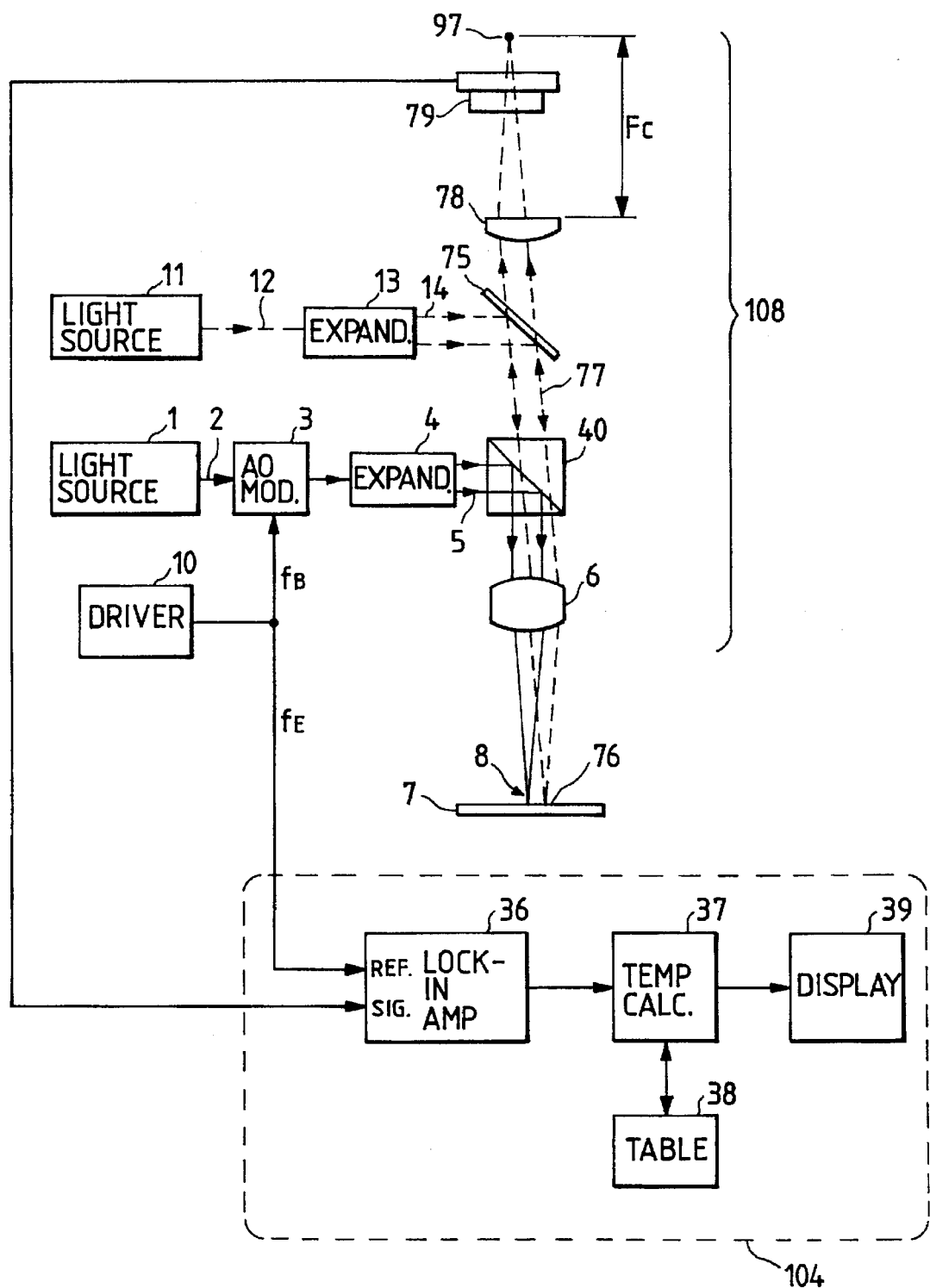
FIG. 9 is a block diagram of a temperature measuring apparatus according to a further embodiment of the present invention.

A temperature measuring apparatus in a further embodiment according to the present invention will be described with reference to FIGS. 9 to 11, wherein FIG. 9 is a block diagram of the temperature measuring apparatus. This temperature measuring apparatus comprises a thermal expansion displacement detecting optical system 108 and a temperature data processing system 104.

While the previous embodiments employ an interferometer for detecting thermal expansion displacement, this embodiment utilizes projection of a probe light beam on an inclined portion of a protrusion formed by periodic thermal expansion displacement and detection of the light beam reflected by the inclined portion of the protrusion.

In the thermal expansion displacement detecting optical system 108, the intensity of a light beam 2 emitted by a light source 1 (wavelength=514.5 nm), such as an Ar laser, is modulated by a modulating frequency $f_E$ by an acoustooptic modulating device 3, the intensity-modulated light beam is expanded by a beam expander 4 to provide an expanded light beam 5, and then the expanded light beam 5 is reflected by a dichroic prism 40, which reflects light beams of wavelengths equal to or below 600 nm and transmits those of wavelengths equal to or above 600 nm, and is concentrated as an exciting light beam on a measuring point 8 on a sample 7 by an objective 6. When the N.A. of the objective 6 is 0.42, the diameter of the spot of the exciting light beam 5 on the sample is about 1.5 μm, which enables the measurement of the temperature of a minute point having an area on the order of square micrometers. As shown in FIG. 10, thermal expansion displacement that varies periodically at a frequency $f_E$ and in an amplitude A is caused at the measuring point 8 by the photothermal displacement effect.

Figure 10:
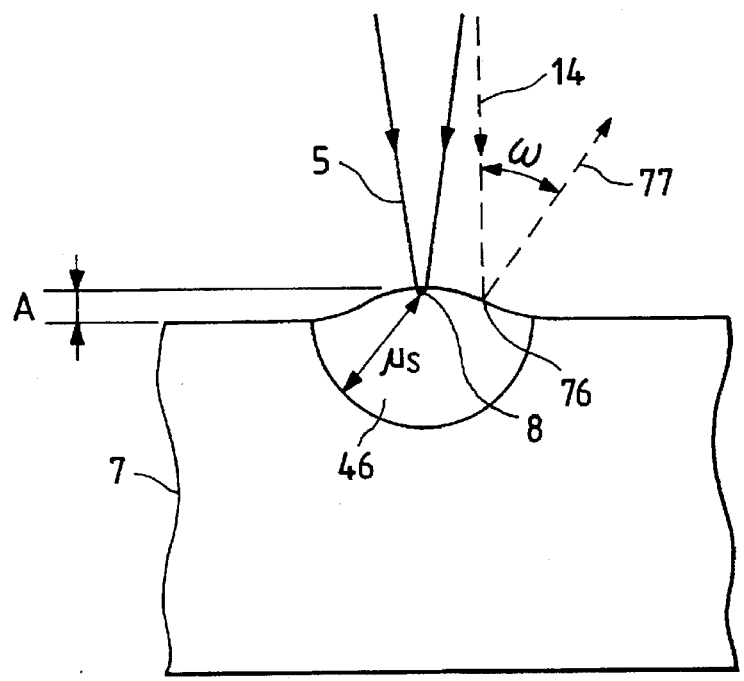
FIG. 10 is a sectional view of a sample, showing a mode of causing periodic thermal expansion displacement by an exciting light beam, and a mode of deflection of a probe light beam in accordance with FIG. 9.
Figure 11:
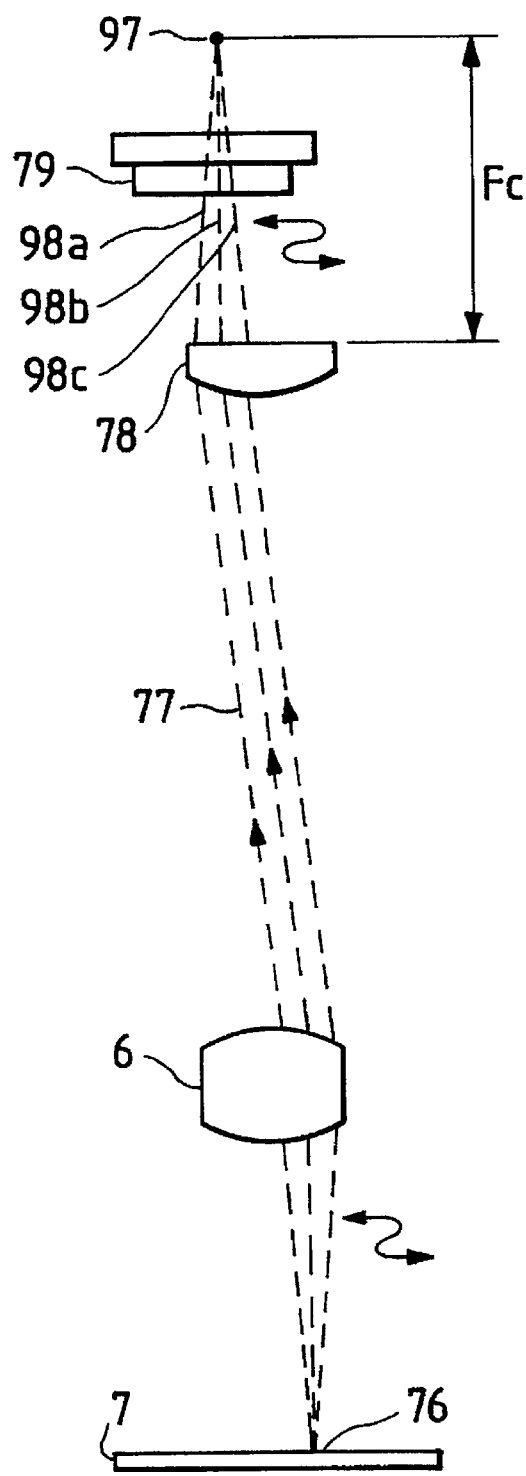
FIG. 11 is a schematic sectional view of an optical system for determining the deflection angle of a reflected probe light beam from the position at which the reflected probe light beam falls in accordance with FIG. 9.

On the other hand, a light beam 12 emitted by a light source 11 (wavelength=633 nm), such as a He-Ne laser, is expanded by a beam expander 13 to provide an expanded light beam 14, the expanded light beam 14 is reflected by a beam splitter 75 and transmitted through the dichroic prism 40, and then the expanded light beam 14 is concentrated as a probe light beam 14 on a point 76 slightly spaced from the temperature measuring point 8 on a sample 7 by the objective 6, as shown in FIG. 10. The probe light beam 14 falls perpendicularly to the surface of the sample 7 on the point 76 in an inclined portion of a protrusion formed by the thermal expansion displacement. The point 76 on the inclined portion is spaced, for example, about half a thermal diffusion length μs from the temperature measuring point 8; that is, at about 9 μm from the temperature measuring point 8 when the modulating frequency $f_E$ is 88 kHz. A reflected probe light beam 77 reverses the optical path of the probe light beam 14 when there is no thermal expansion displacement in the sample. When there is a thermal expansion displacement in the sample, the reflected probe light beam 77 travels along a path deflected at an angle ω to the path of incidence. Therefore, the reflected probe light beam 77 is deflected periodically at an angle ω to the path of incidence by the periodic thermal expansion displacement caused by the exciting light beam 5 having an intensity modulated at the frequency $f_E$. When the N.A. of the objective 6 is 0.42, the diameter of the spot of the probe light beam 14 on the sample is about 1.8 μm, which enables the measurement of a minute spot having an area on the order of square micrometers.

As shown in FIG. 9, the reflected probe light beam 77 is concentrated by a lens 78 on a position detecting device 79 disposed at a distance shorter than the focal length Fc of the lens 78 from the lens 78. The position detecting device 79 detects the deflection angle ω (FIG. 10) as the periodic variation of the position of the reflected probe light beam 77, as shown in FIG. 11, in which the broken lines indicate the axis of the reflected probe light beam 77 deflected at different deflection angles. When the position detecting device 79 is located at the focal point 97 of the lens 78, the reflected probe light beam 77 falls always at the focal point 97 and the variation of the deflection angle cannot be detected. Since the position detecting device 79 is disposed at a distance shorter than the focal length of the lens 78 from the lens 78, the reflected probe light beam 77 falls at positions 98a, 98b and 98c according to the different deflection angles, so that the variation of the deflection angle can be determined from the positions at which the reflected probe light beam 77 falls on the position detecting device 79. The change of the position of the reflected probe light beam 77 on the position detecting device 79 is substantially proportional to the change of the deflection angle ω, and the deflection angle ω is substantially proportional to the thermal expansion displacement A.

Referring to FIG. 9, a beam position detection signal provided by the position detecting device 79 is supplied to a lock-in amplifier 36 included in the temperature data processing system 104, and then the lock-in amplifier 36 determines the amplitude of the beam position displacement varying at the frequency $f_E$ and a phase lag θ included in the beam position detection signal by synchronous detection using the modulating signal of the frequency $f_E$ used for modulating the intensity of the exciting light beam as a reference signal.

As mentioned above, the variation of the position of the reflected probe light beam 77 on the position detecting device 79 is substantially proportional to the deflection angle ω (FIG. 10), and the deflection angle ω is substantially proportional to the thermal expansion displacement A. Accordingly, for example, a reference table showing the relation between the temperature T of the wafer, such as a silicon wafer for fabricating a semiconductor device, and the displacement of the position of the reflected probe light beam theoretically or empirically determined beforehand is stored in a memory or the like instead of the reference table showing the relation between the temperature T of the wafer and the thermal expansion amplitude A, and the temperature T of the wafer can be determined from the measured displacement of the reflected probe light beam. A reference table 38' included in the temperature data processing system 104 shown in FIG. 9 corresponds to the reference table 38' of the first embodiment. The amplitude of the displacement of the reflected probe light beam determined by the lock-in amplifier 36 is sent to a temperature calculating circuit 37, the temperature calculating circuit 37 searches the reference table 38 for a wafer temperature T corresponding to the amplitude of the displacement of the reflected probe light beam, and a display 39 displays the temperature T.

The measuring accuracy of the present embodiment, similarly to that of the first embodiment, can be enhanced by additionally incorporating a surface reflectance measuring optical system 102 and an automatic focus detecting optical system 103 to the temperature measuring apparatus.

The temperature measuring apparatus in the present embodiment, similarly to the temperature measuring apparatus in the first embodiment, is applicable to a semiconductor heat-treating apparatus of a lamp-heating system, a sputtering apparatus and an etching apparatus for the same effect.

The temperature measuring apparatus in the present embodiment, similarly to the temperature measuring apparatus in the first embodiment, may use an exciting light beam having a fixed intensity instead of the intensity-modulated exciting light beam. Additionally, plural light beams or scanning light beams may be utilized to obtain a temperature distribution.

Figure 12:
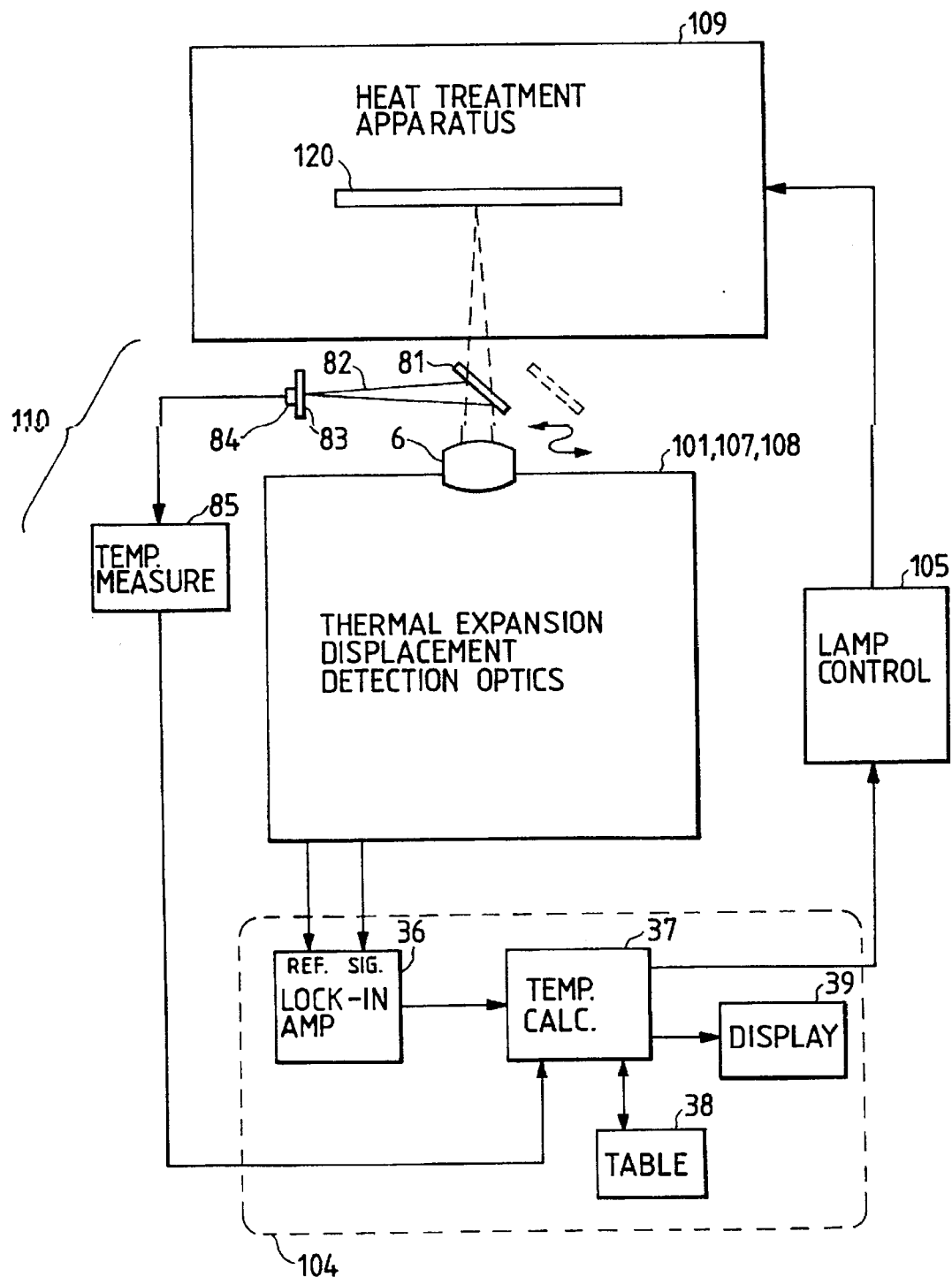
FIG. 12 is a block diagram of a temperature measuring apparatus according to another embodiment of the present invention provided with a temperature calibrating system for calibrating the sensitivity of a detecting system prior to the measurement of the temperature of a sample.

A temperature measuring apparatus in a further embodiment according to the present invention will be described with reference to FIG. 12. FIG. 12 shows a combination of the temperature measuring apparatus in the previously described embodiments and a semiconductor heat-treating apparatus of a lamp-heating system, additionally provided with a temperature calibrating system 110. This temperature measuring apparatus comprises a semiconductor heat-treating apparatus 109, the thermal expansion displacement measuring optical system 101, 107 or 108, a temperature data processing system 104 and a lamp control system 105.

This embodiment is featured by the calibration of the sensitivity of the detecting system by the temperature calibrating system 110 prior to the measurement of the temperature of a silicon wafer 120 to be heat-treated by the semiconductor heat-treating apparatus 109. A movable mirror 81 is inserted in an optical path before starting temperature measurement. An exciting light beam and a probe light beam are projected by the thermal expansion displacement detecting optical system 101, 107 or 108 on a thermally and chemically stable calibrating sample 83, such as a platinum thin film, and a detection signal is processed by a temperature calculating circuit 37 included in the temperature data processing system 104 to determine the temperature of the calibrating sample 83. Meanwhile, the true temperature of the calibrating sample 83 is measured by a thermocouple 84 attached to the back surface of the calibrating sample 83, and a temperature measuring unit 85 provides a temperature signal representing the measured true temperature of the calibrating sample 83. The true temperature thus determined by the temperature measuring unit 85 and the measured temperature determined by the thermal expansion displacement detecting optical system 101, 107 or 108 are compared by the temperature calculating circuit 37, and then the contents of a reference table 38 and the parameters of the temperature calculating circuit 37 are corrected so that the measured temperature coincides with the true temperature. Then, the movable mirror 81 is retracted from the optical path and the measurement of the temperature of the silicon wafer 120 is started.

The sensitivity calibration of the detecting optical system prior to the measurement of the temperature of the sample keeps the sensitivity characteristic of the detecting optical system constant, which improves the accuracy and the reliability of the measured temperature, and the repeatability of measurement.

The temperature measuring apparatus is not limited in its application to the measurement of the temperature of the sample on a semiconductor heat-treating apparatus and may be applied to the measurement of the sample on a film forming apparatus, such as a sputtering apparatus, and an etching apparatus.

Figure 13A:
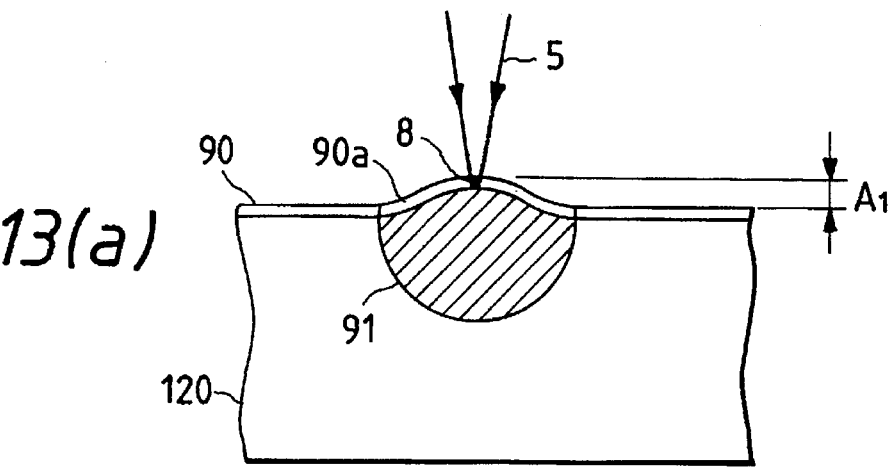
FIGS. 13(a)–13(c) are sectional views of a sample of assistance in explaining the fundamental principle of a temperature measuring apparatus according to yet another embodiment of the present invention.

A temperature measuring apparatus in another embodiment according to the present invention will be described with reference to FIGS. 13(a), 13(b) and 13(c). When any one of the temperature measuring apparatuses in FIGS. 1–11, is applied to the measurement of the temperature of a sample on a semiconductor heat-treating apparatus of a lamp-heating system, a thin film 90 covers a temperature measuring point 8 on the surface of a silicon wafer 120 as shown in FIG. 13(a). Therefore, a thermal expansion displacement $A_1$ is slightly different from a thermal expansion displacement of the measuring point 8 when the measuring point 8 is not coated with the thin film 90 and this small difference is expected to introduce an error in the measurement.

In this embodiment, the temperature measuring apparatus of, for example, the first embodiment is used and an exciting light beam 5 having an intensity modulated by a modulating frequency $f_{E1}$, for example, 60 kHz, is projected on the measuring point 8 as shown in FIG. 13(a) and measures a thermal expansion displacement $A_1$. Then, an exciting light beam 5 having an intensity modulated by a modulating frequency $f_{E2}$, for example, 50 kHz, which is lower than the modulating frequency $f_{E1}$, is projected on the measuring point 8 as shown in FIG. 13(b) and measures a thermal expansion displacement $A_2$. The measured thermal expansion displacements $A_1$ and $A_2$ include the effect of thin films 90a and 90b, respectively. As is apparent from the comparative observation of FIGS. 13(a) and 13(b), the size of a thermal diffusion region when the exciting light beam 5 having an intensity modulated by the modulating frequency $f_{E2}$ is greater than that of a thermal diffusion region when the exciting light beam 5 having an intensity modulated by the modulating frequency $f_{E1}$.

The difference between the thermal expansion displacements $A_1$ and $A_2$ weighted by correcting parameters a and b determined by taking into consideration the parameters defining the sensitivity of the temperature measuring apparatus, and the thermal characteristics of the sample is calculated by using the following expression.

$$\Delta A x = a A_2 - b A_1 \qquad (5)$$

Figure 13B:
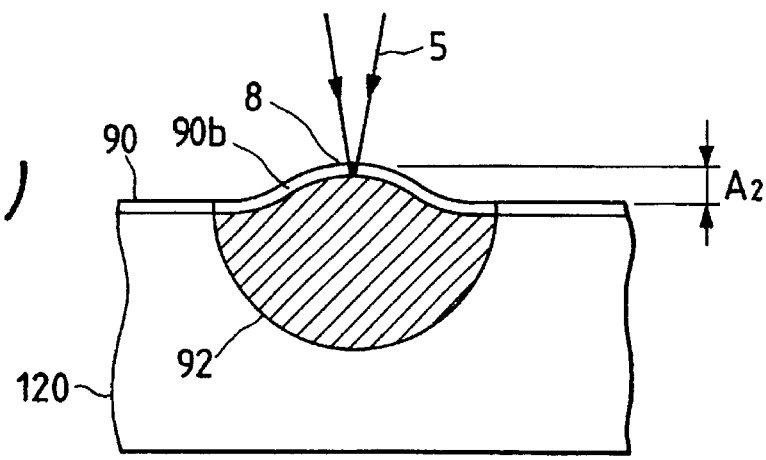
Figure 13C:
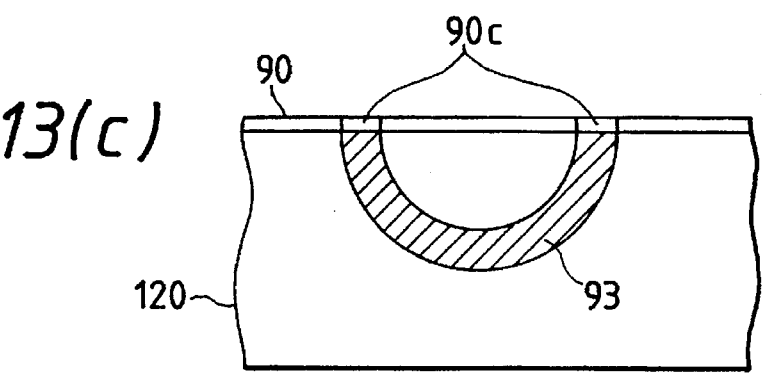

As shown in FIG. 13(c), the physical value $\Delta Ax$ reflects a thermal expansion displacement in a thermal diffusion region 93, i.e., the difference between the thermal diffusion regions 91 [FIG. 13(a)] and 92 [FIG. 13(b)], the area of the thin film 90c is small, and the influence of the thin film 90c is less significant that those of the thin films 90a [FIG. 13(a)] and 90b [FIG. 13(b)]. Similarly to the foregoing embodiments, this embodiment determines the relation between the physical value $\Delta Ax$, i.e., the difference, and the temperature of the wafer beforehand to determine the temperature of the wafer from the calculated difference.

A physical value $\Delta Ay$ that nullifies the influence of the thin film on the thermal expansion displacements $A_1$ and $A_2$ can be calculated by using the following expression.

$$\Delta A y = p A_2 / q A_1 \qquad (6)$$

where p and q are correcting parameters.

The temperature measuring apparatus in the above-noted embodiment is capable of reducing the error due to the thin film formed over the surface of the wafer during temperature measurement.

Naturally, the functions of the temperature measuring apparatus in the above-noted embodiment can be applied to the temperature measuring apparatuses in FIGS. 7–11.

The temperature measuring apparatus in FIGS. 13(a)–13(c) is not limited to application to the semiconductor heat-treating apparatus of a lamp-heating system and may be applied to other semiconductor thin film forming apparatus, such as a sputtering apparatus.

As is apparent from the foregoing description, according to the present invention, a thermal expansion displacement of a measuring point on the surface of a solid sample caused by projecting a light beam having a fixed intensity or a light beam having a variable intensity periodically varying at a frequency on the measuring point in a spot of a diameter on the order of micrometers is measured with high accuracy by light interference or light deflection on the basis of a fact that the thermal expansion displacement is dependent on the thermal conductivity and the linear expansion coefficient of the solid, and the thermal conductivity and the linear expansion coefficient vary according to the local temperature of the solid, and the local temperature of the measuring point is calculated by using the thermal expansion displacement. Accordingly, the temperature of the minute point having an area on the order of square micrometers can be accurately determined through noncontact temperature measurement. The present invention also reduces an error in temperature measurement due to a thin film formed over the surface of a wafer during temperature measurement and enables obtaining of a temperature.

Many different embodiments of the present invention may be constructed without departing from the spirit and scope of the invention. It should be understood that the present invention is not limited to the specific embodiments described in this specification. To the contrary, the present invention is intended to cover various modifications and equivalent arrangements included within the spirit and scope of the claims.

What is claimed is:

1. A temperature measuring method comprising the steps of:
   irradiating at least one measuring point on a surface of a sample at least with one light beam for effecting heating of the sample;
   detecting a displacement of the at least one measuring point on the surface of the sample resulting from thermal expansion of the sample in response to the one light beam impinging thereon and heating the sample and producing a signal indicative of the displacement; and
   determining the temperature of the at least one measuring point of the sample from the signal.

2. A temperature measuring method according to claim 1, wherein the step of irradiating at least one measuring point on the surface of the sample includes irradiating a plurality of measuring points on the surface of the sample, and the step of determining the temperature includes determining the temperature of the plurality of measuring points on the surface of the sample so as to obtain a temperature distribution of the sample.

3. A temperature measuring method according to claim 1, wherein the step of irradiating at least first and second light beams onto the surface of the sample and intensity modulating the first and second irradiated light beams at different frequencies from one another.

4. A temperature measuring method according to claim 3, wherein the step of detecting displacement includes detecting a first displacement in accordance with irradiation by the first light beam and detecting a second displacement in accordance with irradiation by the second light beam, subtracting a signal of the first displacement from the signal of the second displacement, and determining the temperature of a portion of the sample in accordance with the subtracted signal.

5. A temperature measuring method according to claim 1, wherein the steps of irradiating at least with one light beam and detecting include emitting a first light beam from a first light source and intensity modulating the emitted first light beam which irradiates the sample, and emitting a second light beam from a second light source onto the surface of the sample for detecting the displacement resulting from thermal expansion.

6. A temperature measuring method according to claim 1, wherein the step of irradiating at least with one light beam includes emitting a first light beam from a first light source which has a constant intensity.

7. A temperature measuring method according to claim 1, wherein the steps of irradiating at least with one light beam and detecting include emitting a first light beam from a first light source and emitting a second light beam from a second light source, splitting the second light beam into two split second light beams, projecting one of the two split second light beams as a probe light beam onto the at least one measuring point and obtaining a reflected probe light beam therefrom, utilizing the other of the two split second light beams as a reference light beam and interfering the reflected probe light beam and the reference light beam to form an interference light beam, and the step of detecting includes detecting the interference light beam by photoelectric conversion.

8. A temperature measuring method according to claim 1, wherein the steps of irradiating at least with one light beam and detecting include projecting a second light beam emitted by a second light source as a probe light beam on a position slightly spaced from a position on which a first light beam from a first light source is projected, and detecting the deflection of the reflected probe light beam by photoelectric conversion.

9. A temperature measuring method according to claim 1, wherein the steps of detecting the displacement and determining the temperature of the measuring point include providing a relation between the displacement resulting from thermal expansion and a temperature of the sample, and collating the displacement caused by thermal expansion with the provided relation so as to determine the temperature of the at least one measuring point.

10. A semiconductor film forming method comprising the steps of utilizing the temperature measuring method according to claim 1, for measuring the temperature of a semiconductor wafer during processing of the semiconductor wafer to form a thin film over the surface of the semiconductor wafer, and controlling the temperature of the semiconductor wafer on the basis of the measured temperature to control a thickness and a quality of the thin film formed on the semiconductor wafer.

11. A temperature measuring method according to claim 1, wherein the step of irradiating at least with one light beam includes modulating the one light beam at first and second different frequencies.

12. A temperature measuring method comprising the steps of:
   modulating an intensity of a first light beam emitted from a first light source by a first frequency;
   projecting the intensity-modulated first light beam at the first frequency onto at least one measuring point on a surface of a sample to heat the sample;

converting a displacement of the at least one measuring point on the surface of the sample resulting from thermal expansion due to heating of the sample by impingement of the first light beam thereon into an electric signal containing frequency components of the first frequency;

extracting information relating to the frequency components of the first frequency from the electric signal; and determining a temperature of the sample at the at least one measuring point in accordance with the extracted information.

13. A temperature measuring method according to claim 2, wherein the step of converting the displacement into an electric signal includes splitting a second light beam emitted by a second light source into two split second light beams, projecting one of the two split light beams as a probe light beam onto the at least one measuring point and obtaining reflected probe light beam from the at least one measuring point, interfering the reflected probe light beam and the other of the two split second light beams to form an interference light beam, and obtaining the electric signal by photoelectric conversion of the interference light beam.

14. A temperature measuring method according to claim 12, wherein the step of converting the displacement into an electric signal includes projecting a probe second light beam emitted by a second light source at a position slightly spaced from the position on which the intensity-modulated first light beam is incident on the surface of the sample, obtaining a reflected probe light beam, and subjecting the deflection of the reflected probe light beam to photoelectric conversion.

15. A temperature measuring method according to claim 12, wherein the step of determining the temperature of the at least one measuring point includes providing a relation between the temperature of the sample and an amplitude of a frequency component of the displacement resulting from thermal expansion, and collating the amplitude of the frequency component with the relation so as to determine the temperature of the at least one measuring point.

16. A semiconductor film forming method comprising the steps of utilizing the temperature measuring method according to claim 12, for measuring the temperature of a semiconductor wafer during processing of the semiconductor wafer to form a thin film over the surface of the semiconductor wafer, and controlling the temperature of the semiconductor wafer on the basis of the measured temperature to control a thickness and a quality of the thin film formed on the semiconductor wafer.

17. A temperature measuring apparatus comprising:

means for irradiating at least one measuring point on a surface of a sample at least with one light beam to heat the sample;

means for detecting a displacement of the at least one measuring point on the surface of the sample resulting from thermal expansion of the sample in response to the one light beam impinging thereon and heating the sample and producing a signal indicative of the displacement; and means for determining the temperature of the at least one measuring point of the sample from the signal.

18. A temperature measuring apparatus according to claim 17, wherein the means for irradiating at least one measuring point on the surface of the sample includes means for irradiating a plurality of measuring points on the surface of the sample, and the means for determining the temperature includes means for determining the temperature of the plurality of measuring points on the surface of the sample so as to obtain a temperature distribution of the sample.

19. A temperature measuring apparatus according to claim 17, wherein means for irradiating at least with one light beam includes means for irradiating at least first and second light beams onto the surface of the sample and intensity modulating the first and second irradiated light beams at different frequencies from one another.

20. A temperature measuring apparatus according to claim 19, wherein the means for detecting displacement includes means for detecting a first displacement in accordance with irradiation by the first light beam and means for detecting a second displacement in accordance with irradiation by the second light beam, means for subtracting a signal of the first displacement from the signal of the second displacement, and means for determining the temperature of a portion of the sample in accordance with the subtracted signal.

21. A temperature measuring apparatus according to claim 17, wherein the means for irradiating at least with one light beam and the means for detecting include means for emitting a first light beam from a first light source and intensity modulating the emitted first light beam which irradiates the sample, and means for emitting a second light beam from a second light source onto the surface of the sample for detecting the displacement resulting from thermal expansion.

22. A temperature measuring apparatus according to claim 17, wherein the means for irradiating at least with one light beam includes means for emitting a first light beam from a first light source which has a constant intensity.

23. A temperature measuring apparatus according to claim 17, wherein the means for irradiating at least with one light beam and the means for detecting includes means for emitting a first light beam from a first light source and means for emitting a second light beam from a second light source, means for splitting the second light beam into two split second light beams, means projecting one of the two split second light beams as a probe light beam onto the at least one measuring point and obtaining a reflected probe light beam therefrom, utilizing the other of the two split second light beams as a reference light beam and means for interfering the reflected probe light beam and the reference light beam to from an interference light beam, and the means for detecting includes detecting the interference light beam by a photoelectric converter.

24. A temperature measuring apparatus according to claim 17, wherein the means for irradiating at least with one light beam and the means for detecting include means for projecting a second light beam emitted by a second light source as a probe light beam on a position slightly spaced from a position on which a first light beam from a first light source is projected, and means for detecting the deflection of the reflected probe light beam by a photoelectric converter.

25. A semiconductor film forming apparatus comprising the temperature measuring apparatus according to claim 17, for measuring the temperature of a semiconductor wafer during processing of the semiconductor wafer to form a thin film over the surface of the semiconductor wafer, and means for controlling the temperature of the semiconductor wafer on the basis of measured temperature to control the a thickness and a quality of the thin film formed on the semiconductor wafer.

26. A temperature measuring apparatus according to claim 17, wherein the means for irradiating at least with one light beam includes modulating the one light beam at first and second different frequencies.

27. A temperature measuring apparatus according to claim 17, wherein the means for detecting the displacement and means for determining the temperature of the measuring point includes means for storing a relation between the displacement resulting from thermal expansion and a temperature of the sample, and means for collating the displacement caused by thermal expansion with the stored relation so as to determine the temperature of the at least one measuring point.

28. A temperature measuring apparatus comprising:

means for modulating an intensity of a first light beam emitted from a first light source by a first frequency;

means for projecting the intensity-modulated first light beam at the first frequency onto at least one measuring point on a surface of a sample to heat the sample;

means for converting a displacement of the at least one measuring point on the surface of the sample resulting from thermal expansion due to heating of the sample by impingement of the first light beam thereon into an electric signal containing frequency components of the first frequency;

means for extracting information relating to the frequency components of the first frequency from the electric signal; and means for determining a temperature of the sample of at least one measuring point in accordance with the extracted information.

29. A temperature measuring apparatus according to claim 28, wherein the means for converting the displacement into an electric signal includes means for splitting a second light beam emitted by a second light source into two split second light beams, means for projecting one of the two split light beams as a probe light beam onto the at least one measuring point and obtaining a reflected probe light beam from the at least one measuring point, means for interfering the reflected probe light beam and the other of the two split second light beams to form an interference light beam, and means for obtaining the electric signal by photoelectric conversion of the interference light beam.

30. A temperature measuring apparatus according to claim 28, wherein the means for converting the displacement into an electric signal includes means for projecting a probe second light beam emitted by a second light source at a position slightly spaced from the position on which the intensity-modulated first light beam is incident on the surface of the sample, means for obtaining a reflected probe light beam, and means for subjecting the deflection of the reflected probe light beam to photoelectric conversion.

31. A temperature measuring apparatus according to claim 28, wherein the means for determining the temperature of the at least one measuring point includes means for providing a relation between the temperature of the sample and an amplitude of a frequency component of the displacement resulting from thermal expansion, and means for collating the amplitude of the frequency component with the stored relation so as to determine the temperature of the at least one measuring point.

32. A semiconductor film forming apparatus comprising the temperature measuring apparatus according to claim 28, for measuring the temperature of a semiconductor wafer during processing of the semiconductor wafer to form a thin film over the surface of the semiconductor wafer, and means for controlling the temperature of the semiconductor wafer on basis of the measured temperature to control the a thickness and a quality of the thin film formed on the semiconductor wafer.

* * * * *